United States Patent
Yim et al.

(10) Patent No.: US 9,284,266 B2
(45) Date of Patent: Mar. 15, 2016

(54) METHOD FOR SYNTHESIZING RAMALIN AND RAMALIN PRECURSOR BY USING GLUTAMIC ACID DERIVATIVE AND HYDROXY ANILINE OR HYDROXY ANILINE HAVING PROTECTED HYDROXY GROUP

(75) Inventors: Joung Han Yim, Gyeonggi-do (KR); Il Chan Kim, Seoul (KR); Dockyu Kim, Incheon (KR); Se Jong Han, Gyunggi-do (KR); Hyoung Seok Lee, Seoul (KR); Hari Datta Bhattarai, Incheon (KR); Tai Kyoung Kim, Incheon (KR); Keun Sik Kim, Jeollanam-do (KR)

(73) Assignee: KOREA INSTITUTE OF OCEAN SCIENCE AND TECHNOLOGY, Gyeonggi-Do (KR)

( * ) Notice: Subject to any disclaimer, the term of this patent is extended or adjusted under 35 U.S.C. 154(b) by 46 days.

(21) Appl. No.: 14/372,787

(22) PCT Filed: Mar. 26, 2012

(86) PCT No.: PCT/KR2012/002189
§ 371 (c)(1),
(2), (4) Date: Oct. 1, 2014

(87) PCT Pub. No.: WO2013/108959
PCT Pub. Date: Jul. 25, 2013

(65) Prior Publication Data
US 2015/0038733 A1    Feb. 5, 2015

(30) Foreign Application Priority Data
Jan. 19, 2012   (KR) ............... 10-2012-00069366

(51) Int. Cl.
*C07C 261/00*   (2006.01)
*C07C 241/02*   (2006.01)
*C07C 241/04*   (2006.01)
*C07C 269/06*   (2006.01)

(52) U.S. Cl.
CPC ............ *C07C 241/02* (2013.01); *C07C 241/04* (2013.01); *C07C 269/06* (2013.01)

(58) Field of Classification Search
CPC .... C08F 232/08; C08F 222/06; C08F 232/02; C08F 8/14; C07C 241/02; C07C 269/06; C07C 241/04; C07C 243/22; C07C 243/34; C07C 271/22; G03F 7/022; G03F 7/0226; G03F 7/0233; G03F 7/40
See application file for complete search history.

(56) References Cited

U.S. PATENT DOCUMENTS

| | | | |
|---|---|---|---|
| 2010/0086627 | A1 | 4/2010 | Zabrecky |
| 2011/0262374 | A1 | 10/2011 | Yim et al. |
| 2013/0116324 | A1 | 5/2013 | Yim et al. |
| 2013/0211133 | A1* | 8/2013 | Yim ...................... C07C 241/04 562/439 |

FOREIGN PATENT DOCUMENTS

| KR | 10-2010-0052130 A | 5/2010 |
|---|---|---|
| KR | 10-2011-0132938 A | 12/2011 |

OTHER PUBLICATIONS

Ahmadjian, V., "The Lichen Symbiosis", 1993, pp. 1-7, Publisher: John Wiley & Sons, Inc., Published in: New York.
Behera, B., et al., "Determination of antioxidative potential of lichen Usnea ghattensis in vitro", "Lebensm. Wiss. Technol. (LWT)", 2006, pp. 80-85, vol. 39.
Bhattarai, H., et al., "Thin layer chromatography analysis of antioxidant constituents of lichens from Antarctica", "J Nat Med", Jun. 17, 2008, pp. 481-484, vol. 62.
Mueller, K., "Pharmaceutically relevant metabolites from lichens", "Appl Microbiol Biotechnol", May 29, 2001, pp. 9-16, vol. 56.
Paudel, B., et al., "Ramalin, a novel nontoxic antioxidant compound from the Antarctic lichen Ramalina terebrata", "Phytomedicine", Jul. 29, 2011, pp. 1285-1290, vol. 18.

* cited by examiner

*Primary Examiner* — Yevegeny Valenrod
*Assistant Examiner* — Blaine G Doletski
(74) *Attorney, Agent, or Firm* — Hultquist IP; Steven J. Hultquist

(57) ABSTRACT

Disclosed is a method of the synthesis of ramalin. It comprises reacting a glutamic acid derivative, which is prepared using alkylchloroformate, with a hydrazine salt compound, which is prepared from hydroxy aniline, whether protected or not. The synthesis method allows ramalin, excellent in antioxidant and anti-inflammatory activity, to be simply synthesized at stable yield even without use of a highly toxic solvent such as DMF. In addition, the method is cost competitive, and provides ramalin at high efficiency, thus enabling the mass production of ramalin.

12 Claims, 6 Drawing Sheets

METHOD FOR SYNTHESIZING RAMALIN AND RAMALIN PRECURSOR BY USING GLUTAMIC ACID DERIVATIVE AND HYDROXY ANILINE OR HYDROXY ANILINE HAVING PROTECTED HYDROXY GROUP

CROSS-REFERENCE TO RELATED APPLICATIONS

This application is a U.S. national phase under the provisions of 35 U.S.C. §371 of International Patent Application No. PCT/KR12/02189 filed Mar. 26, 2012, which in turn claims priority of Korean Patent Application No. 10-2012-00069366 filed Jan. 19, 2012. The disclosures of such international patent application and Korean priority patent application are hereby incorporated herein by reference in their respective entireties, for all purposes.

TECHNICAL FIELD

The present invention relates to a method of the synthesis of ramalin. More particularly, the present invention relates to a method of synthesizing ramalin by reacting a glutamic acid derivative which is prepared using alkylchloroformate, with hydroxy aniline, or protected hydroxy aniline.

BACKGROUND ART

A lichen, resembling a non-flowering plant, is a composite organism consisting of a fungus (myobiant), and a photosynthetic partner (photobiant) growing together in a symbiotic relationship. The photobiant is usually either or both of an alga and cyanobacterium. In lichens, fungi contain thalli or typical metabolites (Ahmadjin V., *The lichen symbiosis*, Wiley, New York, pp. 1-6, 1993). Since lichens are difficult to collect in a sufficient amount from nature and their mass production has not yet been established, they are unsatisfactorily studied, compared to higher vegetation.

However, active studies on lichens are now being done and there has appeared an improvement in tissue culture, mass culture, and biochemical analysis for lichens (Behera, B. C. et al., *Lebensm. Wiss. Technol.*, 39:805, 2006). From lichens have been isolated a variety of compounds with biological activities, such as cytotoxicity, fungicidal activity, anti-microbial activity, and antioxidant activity, as exemplified by fatty acids, depside and depsidones, debenzofurans, diterpenes, anthraquinones, naphtoquinones, usninic acid, pulvinic acids, xanthones and epidithiopiperazinediones (Muller, K., *Appl. Microbiol. Biotechnol.*, 56:9-16, 2001).

*Ramalina terebrata*, a variety of lichen, grows wildly, forming colonies on King George Island, Antarctica, and can be easily collected from various places on the island. Previously, the present inventors studied the Antarctic lichen *Ramalina terebrata* and succeeded in isolating therefrom a novel compound, named ramalin, with excellent antioxidant activity (Korean Patent Publication No. 10-2010-0052130). In addition, ramalin was reported to exhibit excellent anti-inflammatory activity (Korean Patent Application No. 10-2010-005255).

The findings of its excellent antioxidant and anti-inflammatory activities add necessity to the mass production of ramalin. However, the conventional isolation method of ramalin from *Ramalina terebrata* using methanol (Korean Patent Publication No. 10-2010-0052130) is problematic in terms of cost and time due to the low growth rate characteristic of the Antarctic lichen, difficulty in mass collection from nature, and a very small content in *Ramalina terebrata*.

Leading to the present invention, intensive and thorough research into the novel chemical synthesis of ramalin which is of a simple process and is cost competitive resulted in the finding that ramalin can be simply produced with a high yield by reacting a glutamic acid derivative prepared from alkylchloroformate with a hydrazine salt compound prepared from hydroxy aniline or protected hydroxy aniline The information described in the Background Art Section is to enhance the understanding of the background of the present invention, and may not be information on the prior art already known to those having ordinary skill in the art to which the present invention pertains.

SUMMARY OF THE INVENTION

It is an object of the present invention to provide a novel method of producing ramalin in a cost-competitive and simple manner with a high yield.

To achieve the above object, the present invention provides a method of synthesizing ramalin, represented by the following Chemical Formula 1, comprising reacting a glutamic acid derivative represented by the following Chemical Formula 2 with a hydrazine salt compound represented by the following Chemical Formula 3 to give an intermediate represented by the following Chemical Formula 4; and hydrogenating the compound of Chemical Formula 4 to ramalin:

[Chemical Formula 1]

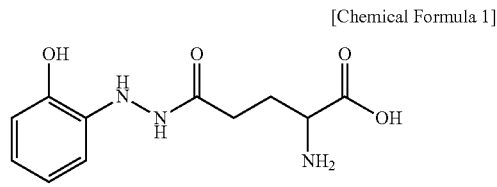

[Chemical Formula 2]

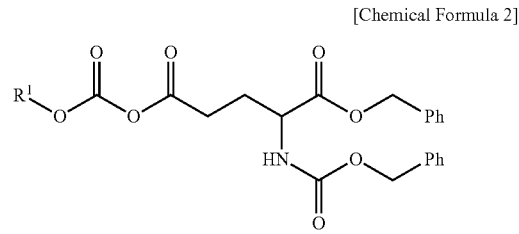

[Chemical Formula 3]

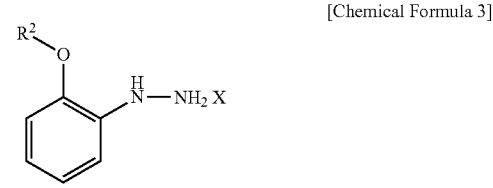

[Chemical Formula 4]

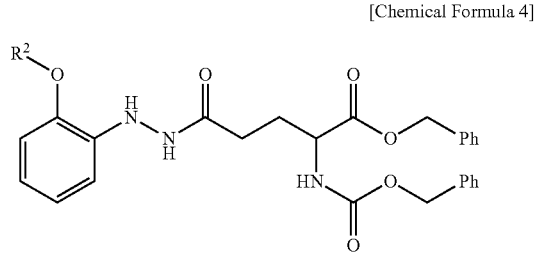

wherein
R1 is alkyl;
R2 is a hydrogen or a protecting group of a hydroxy group; and
X is an acid.

Also, the present invention provides a method of synthesizing a ramalin precursor, comprising reacting a glutamic acid derivative represented by the following Chemical Formula 2 with a hydrazine salt compound represented by the following Chemical Formula 3:

[Chemical Formula 2]

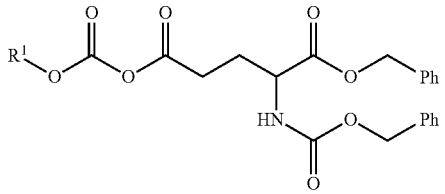

[Chemical Formula 3]

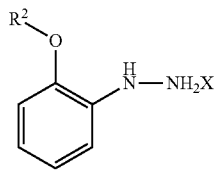

[Chemical Formula 4]

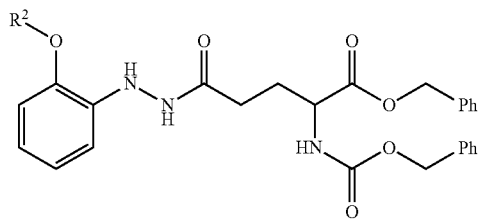

wherein,

R1 is alkyld;

R2 is hydrogen or a hydroxy protecting group;

X is an acid.

Further, the present invention provides a method of synthesizing a compound represented by Chemical Formula 16, comprising reacting an amino acid derivative represented by the following Chemical Formula 17 with a hydrazine salt compound represented by the following Chemical Formula 18:

[Chemical Formula 16]

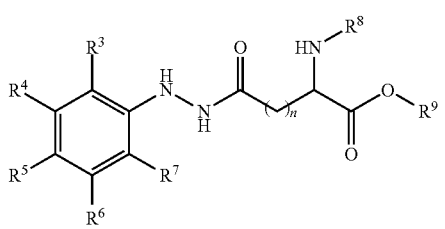

[Chemical Formula 17]

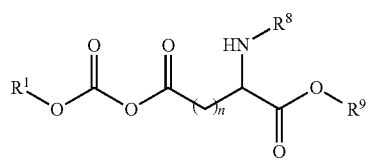

[Chemical Formula 18]

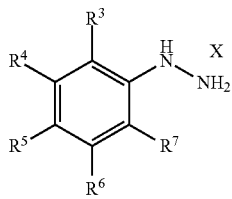

wherein,

R3, R4, R5, R6, or R7 is hydrogen, a hydroxy group, or a hydroxyl alkyl group;

R8 is hydrogen, an alkyl group, or an acyl group;

R9 is hydrogen or an alkyl group;

n is 1, 2, 3, 4 or 5.

Other features, advantages, and embodiments of the present invention will be obvious from the following detailed description and the accompanying claims.

DETAILED DESCRIPTION AND PREFERRED EMBODIMENTS

Figure 1:
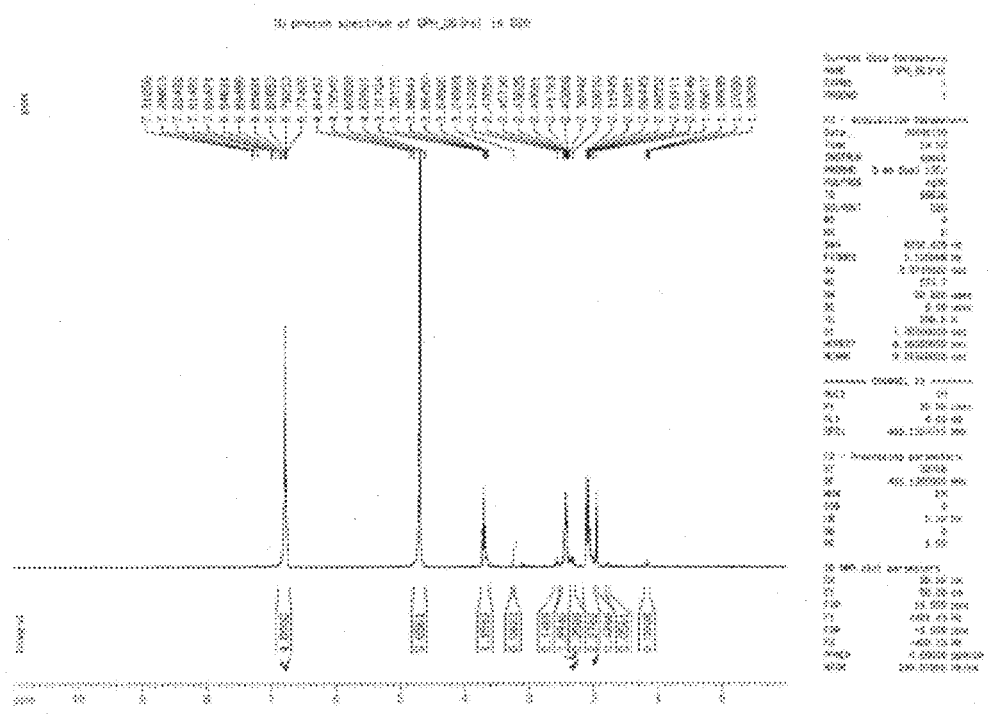
FIG. 1 is an H-NMR spectrum of the ramalin synthesized in Example 1.

Unless defined otherwise, all the technical and scientific terms used in the specification have the same meanings as understood to those skilled in the art to which the present invention pertains. Generally, the nomenclature used in the specification is well known in the art and found in typical practice.

In accordance with an aspect thereof, the present invention addresses a method of synthesizing ramalin, comprising:

(a) reacting a glutamic acid derivative represented by the following Chemical Formula 2 with a hydrazine salt compound represented by the following Chemical Formula 3 to give a compound represented by Chemical Formula 4; and (b) hydrogenating the compound of Chemical Formula 4 to afford the ramalin of Chemical Formula 1:

[Chemical Formula 1]

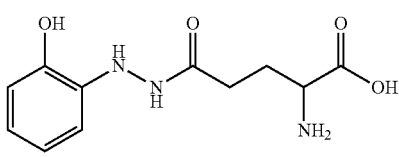

-continued

[Chemical Formula 2]

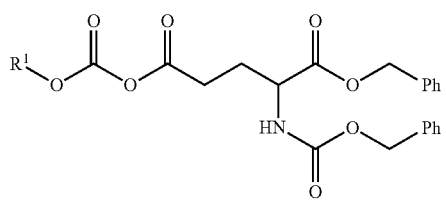

[Chemical Formula 3]

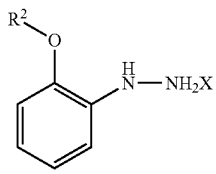

[Chemical Formula 4]

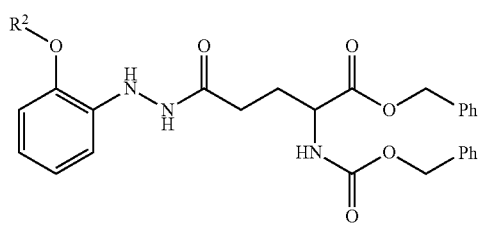

wherein,
$R^1$ is alkyl;
$R^2$ is hydrogen or a hydroxy protecting group; and
X is an acid.

Ramalin according to the present invention is an antioxidant compound first discovered and isolated from the Antarctic lichen *Ramalina terebrata*, and was found to have a molecular weight of 254.1141, as measured by high-resolution ES-MS, and a molecular formula of $C_{11}H_{16}N_3O_4$ possessing the structure of Chemical Formula 1. As implied by the name, ramalin originates from *Ramalina terebrata*.

In the present invention, research has been directed towards the chemical synthesis of ramalin, instead of isolation and extraction, culminating in the development of a simple process in which ramalin can be synthesized by reacting a glutamic acid derivative with a hydrazine salt compound, followed by hydrogenation.

For use in the present invention, the glutamic acid derivative has the structure represented by the following Chemical Formula 2. Preferably, the glutamic acid derivative of Chemical Formula 2 may be prepared by activating a glutamic acid derivative of Chemical Formula 5 with alkylchloroformate having the structure of $R^1$—O—CO—Cl in a mixed anhydride coupling mechanism, the glutamic acid derivative of Chemical Formula 5 being derived from glutamic acid by protecting the amino group with a carbobenzyloxy group and esterifying the alpha carboxyl group with a benzyl group.

[Chemical Formula 2]

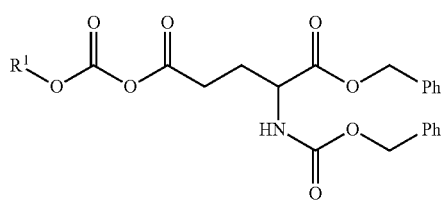

[Chemical Formula 5]

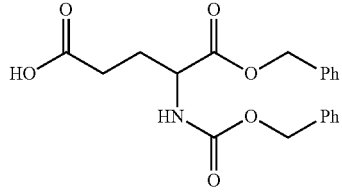

In the alkylchloroformate, $R^1$ corresponds to $R^1$ of Chemical Formula 2, and is alkyl. So long as it is alkyl, any group may be employed in the art. Examples of $R^1$ include, but are not limited to, methyl, ethyl, propyl, isopropyl, butyl, isobutyl, pentyl, hexyl, heptyl, octyl, 2-ethylhexyl, substituted alkyl, and cycloalkyl. Preferred is ethyl because it can be industrially purchased in a large amount and is easy to handle.

After the coupling of the glutamic acid derivative of Chemical Formula 5 with alkylchloropromate, the benzyl group is deprotected, and tetrahydrofuran (THF) or acetonitrile (MeCN) is used as a crystallization solvent in one embodiment of the present invention. THF was measured to increase the final production yield of ramalin by about 13 to 16%. The crystallization solvent used in the reaction may be any one that is known in the art. Preferred is THF.

Subsequently, the activated glutamic acid derivative of Chemical Formula 2 is subjected to a coupling reaction with the hydrazine salt compound of the following Chemical Formula 3. The hydrazine salt of Chemical Formula 3 may be prepared by adding an acid to protected hydroxy aniline to give an acid salt, followed by coupling with an azo compound, and reducing. An alternative approach is a non-protecting process in which the hydroxy aniline of Chemical Formula 6 is added with an acid (hydrochloric acid) to give an acid salt (hydrochloride salt) which is then reacted as illustrated in Reaction Scheme 1-2.

[Chemical Formula 6]

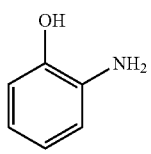

[Chemical Formula 3]

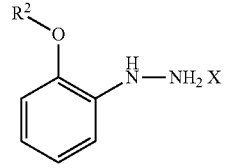

In one embodiment of the present invention, as illustrated in Reaction Schemes 1-1 and 1-2, the hydroxy aniline of Chemical Formula 6 is treated with HCl gas, and the resulting adduct is dissolved in an alcohol, such as ethanol, and coupled with an azo compound to give the intermediate of Chemical Formula 8 which is then reduced with toluene sulfonic acid (TsOH) and tin chloride to afford the hydrazine tosylate of Chemical Formula 9. In these reaction schemes, the hydroxy aniline is employed without protecting the hydroxy group.

[Reaction Scheme 1-1]

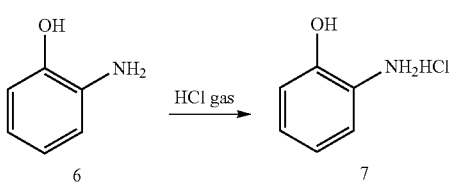

[Reaction Scheme 1-2]

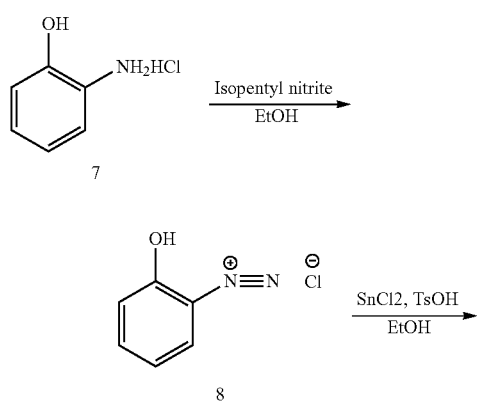

A reaction between the hydrazine salt and the glutamic acid derivative activated in a mixed anhydride coupling mechanism produces ramalin with a purity of 97% or higher. Particularly, even upon scaling up, this protection-free route of the method according to the present invention can produce ramalin at a mean yield of about 50%, and allows for the isolation of ramalin with a purity of 97% or higher.

As elucidated above, the protection-free route is 2 to 3 process steps less and thus is more advantageous in terms of production cost than the protection route because the latter requires 2 to 3 process steps for making the protected starting material.

On the other hand, the hydrazine salt compound of Chemical Formula 3 is characterized by the hydroxy protecting group $R^2$. So long as it protects a hydroxy group, any protecting group may be used in the present invention. Preferable is a benzyl group. The hydroxy protecting group is removed upon hydrogenation reaction in a subsequent step.

In another embodiment of the present invention, the compound of Chemical Formula 12 in which the hydroxy aniline is protected at the hydroxy with a benzyl group is employed to produce ramalin at a mean yield of about 90~92%. That is, the protection route using protected hydroxy aniline may allow for the production of ramalin at very high yield.

[Chemical Formula 12]

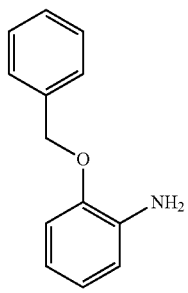

In the present invention, no particular limitations are imparted to the acid that participates in the formation of the hydrazine salt of Chemical Formula 3 if it allows for the formation of a hydrazine salt capable of coupling with the activated glutamic acid derivative of Chemical Formula 2. Examples of the acid include hydrochloric acid, bromic acid, iodic acid and p-toluenesulfonic acid.

Also, the ramalin precursor synthesized according to the present invention is provided. Hence, contemplated in accordance with another aspect of the present invention is a method of synthesizing a ramalin precursor. This method comprises reacting a glutamic acid derivative represented by the following Chemical Formula 2 with a hydrazine salt compound represented by the following Chemical Formula 3 to afford the ramalin precursor of Chemical Formula 4:

[Chemical Formula 2]

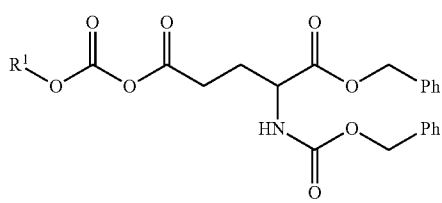

[Chemical Formula 3]

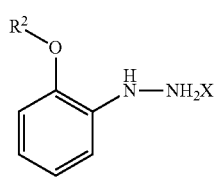

[Chemical Formula 4]

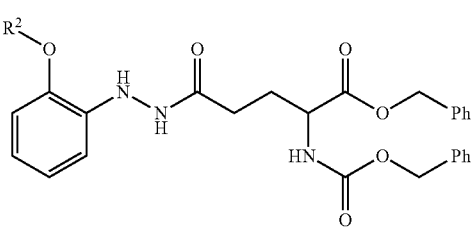

wherein,
$R^1$ is alkyl;
$R^2$ is hydrogen or a hydroxy-protecting group; and
X is an acid.

In accordance with a further aspect thereof, the present invention addresses a method of synthesizing a compound represented by the following Chemical Formula 16, comprising an amino acid derivative represented by the following Chemical Formula 17 with a hydrazine salt compound represented by the following Chemical Formula 18:

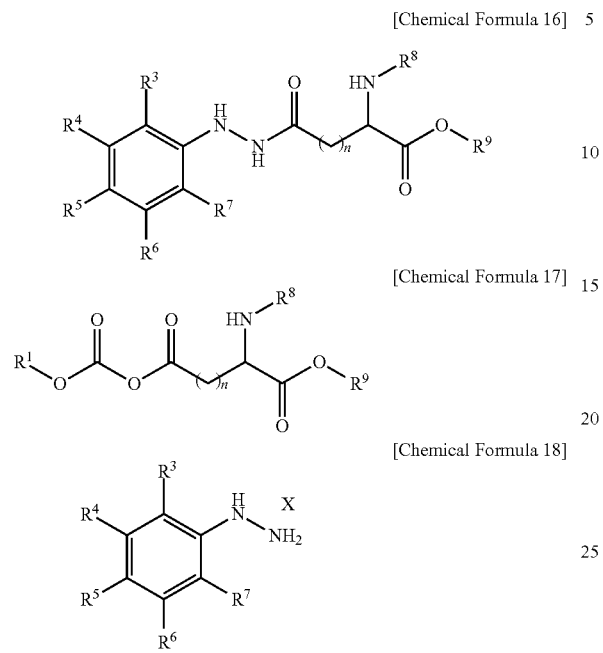

[Chemical Formula 16]

[Chemical Formula 17]

[Chemical Formula 18]

wherein, $R^3$, $R^4$, $R^5$, $R^6$, and $R^7$ are each independently hydrogen, a hydroxyl group or a hydroxyl alkyl group;

$R^8$ is hydrogen, an alkyl group or an acyl group;

$R^9$ is hydrogen or an alkyl group; and n is 1, 2, 3, 4 or 5.

Here, the amino acid derivative is an aspartic acid derivative for n=1, a glutamic acid derivative for n=2, a 2-aminoadipic acid derivative for n=3, a 2-aminopimelic acid derivative for n=4, and a 2-aminooctanedioic acid derivative for n=5.

A better understanding of the present invention may be obtained through the following example(s) which are set forth to illustrate, but are not to be construed as limiting the present invention.

Example 1

Synthesis of Ramalin 1

1-1: Preparation of Hydrazine Salt

[Reaction Scheme 1-1]

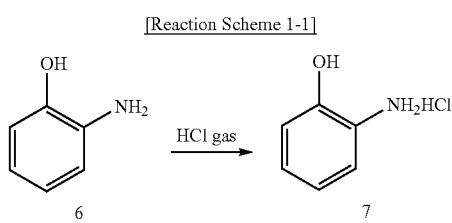

In a 1-liter 4-neck flask, 50 g (0.46 mol) of the compound of Chemical Formula 6 (2-amino phenol) was completely dissolved in 500 ml (11.5 mol) of methanol (MeOH) with vigorous stirring.

To a separate 500 ml flask equipped with a dropping funnel was placed 134 g (2.3 mol) of NaCl, and the dropping funnel was filled with 113 g (1.15 mol) of conc. sulfuric acid ($H_2SO_4$). As $H_2SO_4$ was slowly added from the funnel, HCl gas was generated. The HCl gas was introduced into the 1-L flask while stirring.

After completion of gas generation, the separate 500 ml flask was removed, and stirring was continued for 15 hrs in the HCl gas-injected reactor.

Then, the reactor was purged with $N_2$, followed by vacuum concentration to evaporate about ¾ (400 ml) of the solvent. Ethyl acetate (EA) (1 L) was added to form a precipitate while stirring for 30 min or longer.

The precipitate was an HCl salt of 2-aminophenol, and washed with 200 ml of a mixture of ethyl acetate (EA) and hexane (3:7), and dried in a vacuum to give 60 g of the compound of Chemical Formula 7 (yield: 90%).

[Reaction Scheme 1-2]

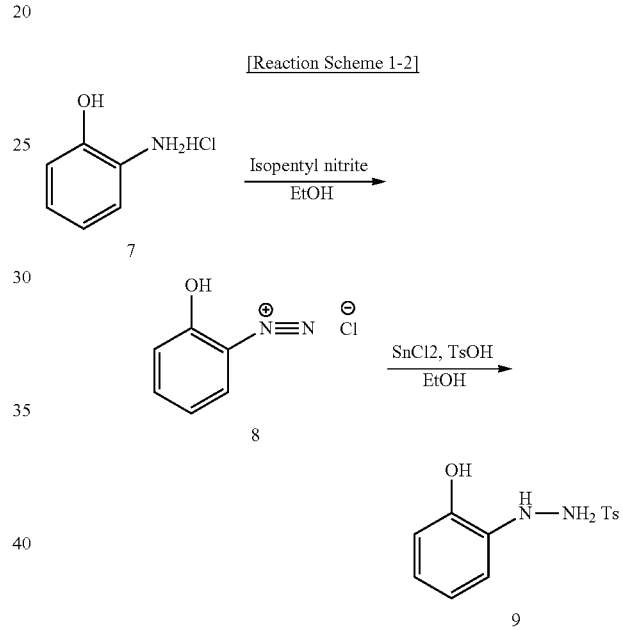

In a 1 L flask on an ice bath, 60 g (0.41 mol) of the compound of Chemical Formula 7 was completely dissolved in 300 ml of ethanol (EtOH) by stirring while the temperature of the flask was kept at −5~0° C.

A solution of 55.3 g (0.41 mol) of isopentyl nitrite in 200 ml of ethanol was added to the flask and stirred for 0.5~1.0 hr to give a diazonium salt solution.

In a separate 2 L flask equipped with a mechanical stirrer on an ice bath, 156.3 g (0.82 mol) of $SnCl_2$, 78.4 g (0.41 mol) of p-toluenesulfonic acid (TsOH), and 500 ml of EtOH 500 ml were mixed by stirring.

While the 2 L flask was kept at 0~5° C., the diazonium salt solution was slowly added to the flask and reacted over 1 hr or longer.

After completion of the reaction, 500 ml of ethyl ether ($Et_2O$) was added to the reaction mixture and stirred for 10 min to form precipitates. After filtration, the cake thus obtained was further washed with 200 ml of ethyl acetate (EA) and 400 ml of hexane to afford 98 g of hydrazine salt of Chemical Formula 9 (Yield: 80%).

1-2: Preparation of Glutamic Acid Derivative and Synthesis of Ramalin

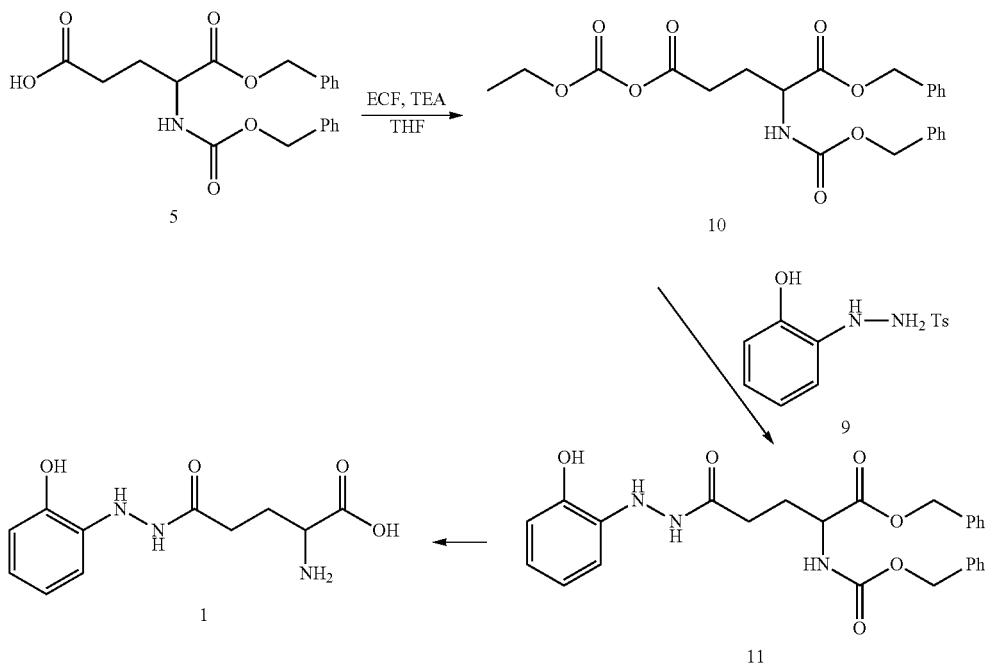

[Reaction Scheme 1-3]

In a 500 ml flask on an ice bath, 30 g (0.08 mol) of the compound of Chemical Formula 5 (N-Carbobenzyloxy-L-Glutamic acid alphabenzyl ester, reagent grade) was completely dissolved in 150 ml of tetrahydrofuran (THF) by stirring, while the flask was kept at −5~0° C.

A solution of 8.2 g (0.08 mol) of triethylamine (TEA) in 30 ml of THF was slowly added over 20~30 min to the flask, and further stirred for an additional 0.5~1.0 hr while the flask was kept at −5° C.

A solution of 8.8 g (0.08 mol) of ethylchloroformate (ECF) in 50 ml of THF was slowly added to the flask and allowed to react for 2.0 hrs or longer while the flask was kept at −10~5° C. (solution A).

In a separate 1 L flask on an ice bath, 25.2 g (0.085 mol) of the hydrazine salt of Chemical Formula 9, 17.0 g (0.16 mol) of TEA, 200 ml of THF, and 60 ml of $H_2O$ were mixed while the flask was maintained at −5° C.

The solution A prepared above was slowly added to the 1 L flask, and the temperature of the flask was elevated to room temperature to allow a reaction for 20 hrs or longer.

After completion of the reaction, THF was removed by vacuum distillation, and 500 ml of ethyl acetate (EA) and 200 ml of $H_2O$ was added and stirred for 10 min to form two layers. The organic layer (EA) was withdrawn, and washed with 5% HCl, and then once with distilled water, followed by vacuum concentration.

Figure 2:
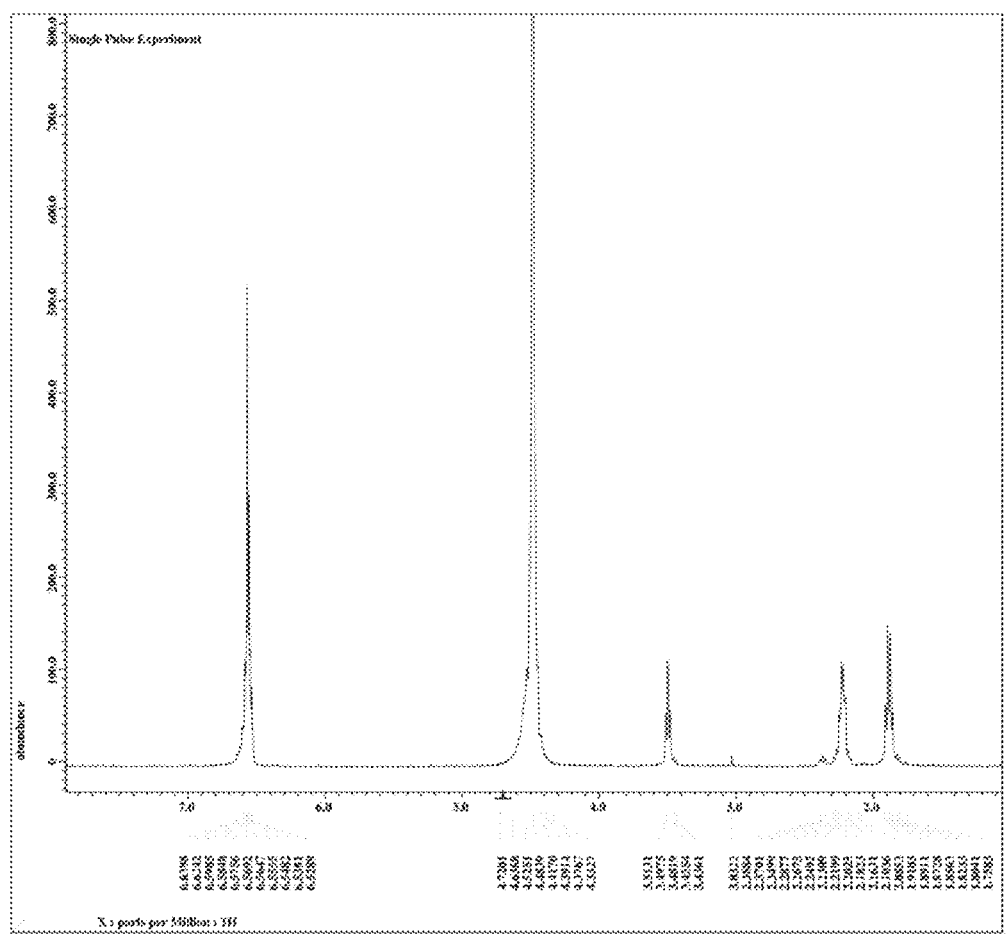
FIG. 2 is an H-NMR spectrum of natural ramalin isolated from *Ramalina terebrata*.

As a result, an oily concentrate was obtained, and dissolved in 250 ml of methanol (MeOH). This solution was fed to a pressure reactor at which a hydrogenation reaction was conducted at a hydrogen pressure of 1~2 atm in the presence of 3~5 g of 10% Pd/C. This hydrofenation resulted in deprotecting the benzyl group. When the hydrogenation was conducted for 20 hrs or longer, the catalyst was filtered off through a cellite filtration aid. The catalyst layer left as a filtration cake was washed with methanol, mixed with the filtrate, and concentrated in a vacuum. In this regard, the evaporation of MeOH was carried out only until the solid started to appear (about ⅘ of MeOH was removed), and MeCN (or THF) was added to the residue to crystallize the product. Subsequently, the crystal was filtered, washed with acetonitrile (MeCN), and dried at room temperature in a vacuum to afford ramalin (Chemical Formula 1) as an off-white solid (12.4 g, total yield 61%). HPLC analysis (condition: Column: Capcellpak C18, Mobile=MeCN:$H_2O$ (0.1% TFA), UV wavelength=220 nm, Flow=0.5 ml/min) exhibited that the ramalin had a purity of 97% or higher. This synthetic product was found to coincide with natural ramalin, as measured by H-NMR analysis. FIG. 1 is H-NMR data for the synthetic ramalin of Chemical Formula 1 while FIG. 2 is H-NMR data for natural ramalin.

1-3: Results According to Crystallization Solvent

Ramalin was synthesized in the same manner as in Examples 1-1 and 1-2, with the exception that kinds of the crystallization solvents or amounts of the glutamic acid derivative of Chemical Formula 5 were changed. The ramalin this obtained was measured for yield and purity, and the results are summarized in Table 1 below.

TABLE 1

Results of Ramalin Synthesis with Various Crystallization Solvent Post Coupling/Hydrogenation/Concentration

| Test No. | Quantity (g) | | Crystallization Solvent | Yield (%) | Purity (HPLC area %) |
|---|---|---|---|---|---|
| | Chemical Formula 5 | Product (Chemical Formula 1) | | | |
| Test-1 | 50 | 15 | MeOH/MeCN | 45 | 97.35 |
| Test-2 | 100 | 32 | MeOH/MeCN | 47 | 96.18 |
| Test-3 | 150 | 48 | MeOH/MeCN | 47 | 97.34 |
| Test-4 | 150 | 61 | MeOH/THF | 60 | 96.23 |

TABLE 1-continued

Results of Ramalin Synthesis with Various Crystallization
Solvent Post Coupling/Hydrogenation/Concentration

| | Quantity (g) | | | | |
|---|---|---|---|---|---|
| Test No. | Chemical Formula 5 | Product (Chemical Formula 1) | Crystallization Solvent | Yield (%) | Purity (HPLC area %) |
| Test-5 | 100 | 41 | MeOH/THF | 61 | 97.13 |
| Total | 550 g | 197 g | | Mean: 52.5% | |

Even upon scaling up, ramalin was stably synthesized at a mean yield of about 50% or higher, and with a purity of about 97%. Particularly, the use of THF as a solvent increased the yield by about 13 to 16%.

Example 2

Synthesis of Ramalin 2

2-1: Preparation of Hydrazine Salt

[Reaction Scheme 2-1]

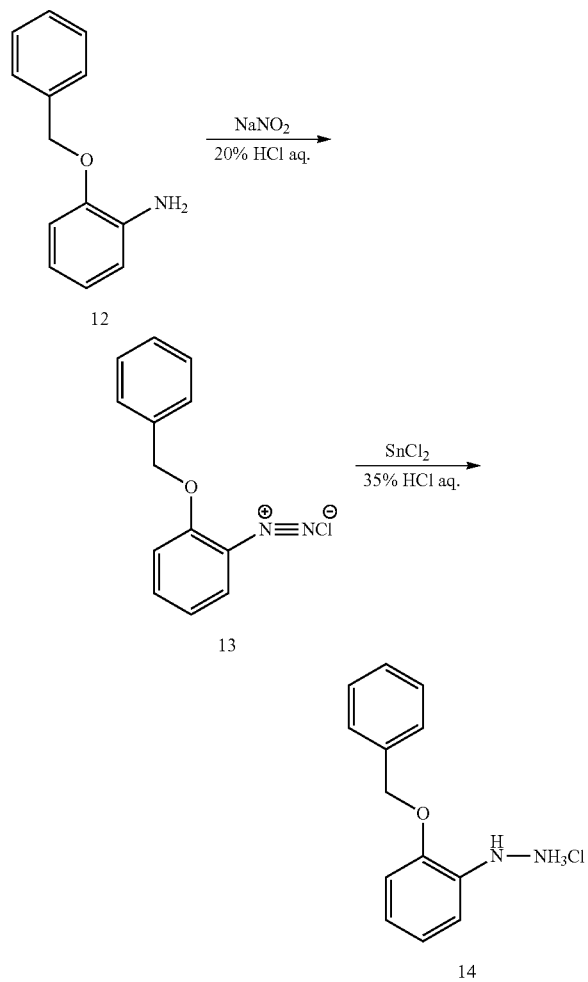

In a 3 L reactor equipped with a stirrer, a thermometer, and a condenser, 85.0 g (0.3606 mol) of the compound of Chemical Formula 12 was dissolved in 1000 ml of distilled water by stirring. A solution of 39.81 g (0.5770 mol) of $NaNO_2$ in 300 ml of $H_2O$ was loaded to a dropping funnel. The 3 L reactor was cooled to 0° C., and the $NaNO_2$ solution was slowly added to the reactor over about 1 hr under the same temperature condition. After completion of the addition, stirring was continued for about 1 hr at the same temperature.

A solution of 225.61 g of $SnCl_2$ in 6M HCl was loaded to a dropping funnel. At the same temperature, the $SnCl_2$/HCl solution was added over about 2 hrs from the dropping funnel, followed by reacting them for an additional 2 hrs. The resulting reaction mixture was adjusted to a pH of 11 or higher using 12.5 M NaOH. After neutralization, extraction with 800 ml of ethyl ether was carried out twice. The $H_2O$ layer was discarded, and the pooled ether layer was dehydrated and fed with HCl gas to give a hydrochloride salt. It was washed with n-hexane, and dried to obtain the hydrazine salt of Chemical Formula 14.

The material balance of the reagents used is as follows.

TABLE 2

Material Balance of Reagents and Theoretical
Yield of Chemical Formula 14

| | MW | QTY | Moles |
|---|---|---|---|
| Chemical Formula 12 | 235.7 | 85.0 | 0.3606 |
| $H_2O$ | 18.0 | 1000 mL | |
| $NaNO_2$ | 69.0 | 39.81 | 0.5770 |
| $H_2O$ | 18.0 | 300 mL | |
| $SnCl_2$ | 189.61 | 225.61 | 1.1899 |
| HCl 6M | 36.5 | 800 mL | |
| 25M NaOH | 40.0 | | |
| Chemical Formula 14 | 250.72 | 90.41 | 0.3606 |

The experiment described above was repeated 12 more times, and the results are summarized in Table 3, below.

TABLE 3

Results of 13 Rounds of Experiment

| EXP. No. | 100% Yield wt. (g) | Product Weight (g) | Yield (%) |
|---|---|---|---|
| 001 | 36.17 | 36.2 | 69.1 |
| 002 | 67.02 | 48.0 | 71.6 |
| 003 | 67.02 | 49.2 | 73.4 |
| 004 | 106.38 | 84.0 | 78.9 |
| 005 | 106.38 | 84.1 | 79.0 |
| 006 | 106.38 | 84.3 | 79.2 |
| 007 | 106.38 | 79.0 | 73.5 |
| 008 | 106.38 | 85.0 | 80.0 |
| 009 | 106.38 | 84.4 | 79.3 |
| 010 | 106.38 | 83.6 | 78.5 |
| 011 | 106.38 | 80.0 | 76.0 |
| 012 | 106.38 | 82.0 | 77.0 |
| 013 | 90.41 | 72.0 | 79.6 |

Figure 3:
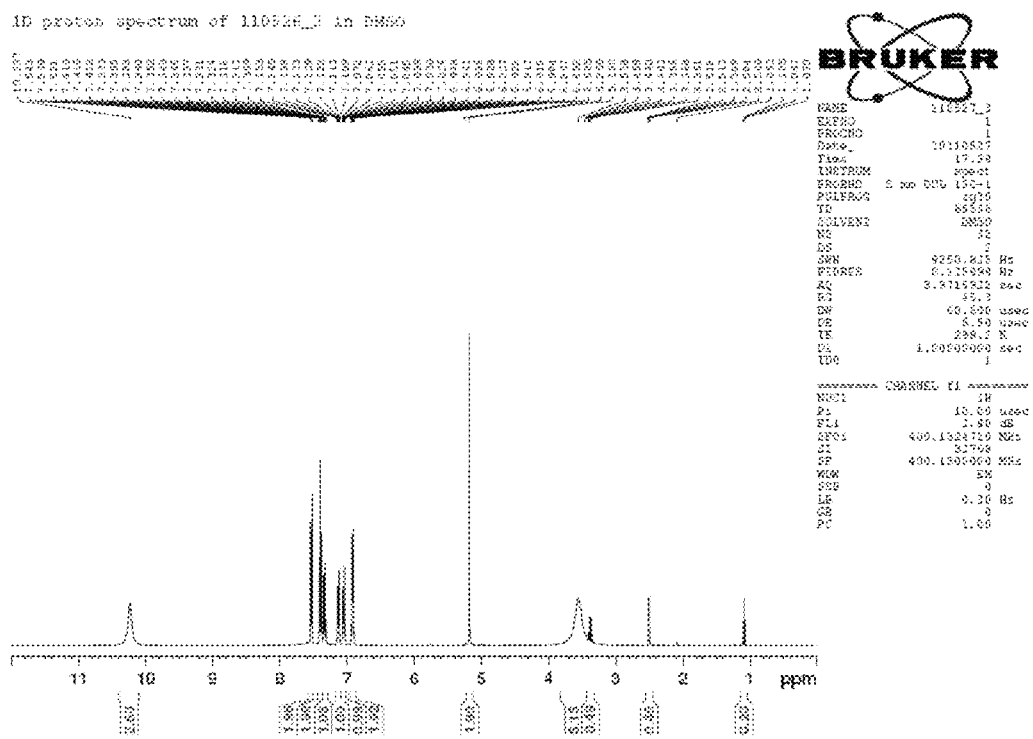
FIG. 3 is an $^1$H-NMR spectrum of the compound of Chemical Formula 14.

As shown in Table 3, the hydrazine salt of Chemical Formula 14 was prepared with a mean yield of 75~80%, and the results were identified by HPLC and $^1$H-NMR (FIG. 3).

2-2: Preparation of Glutamic Acid Derivative and Ramalin

[Reaction Scheme 2-2]

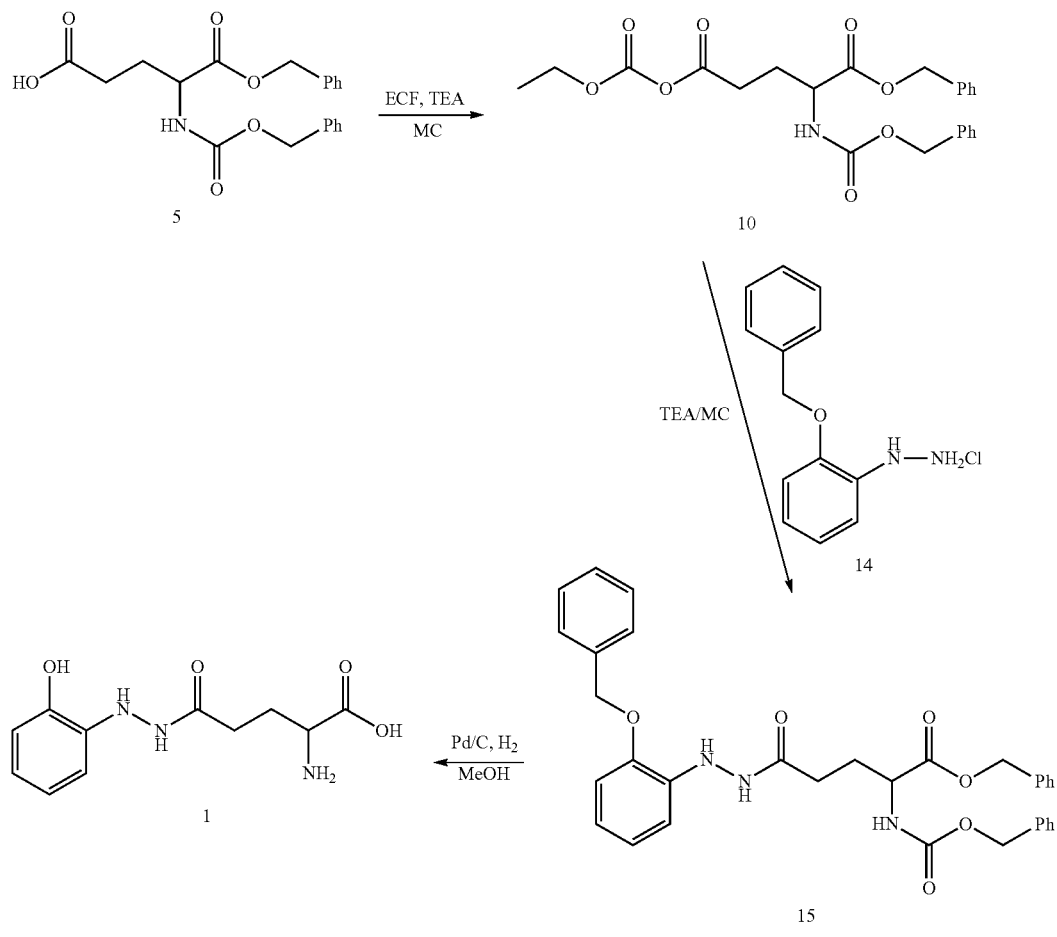

In a 3 L reactor equipped with a stirrer, a thermometer, and a condenser, 92.58 g (0.2493 mol) of the compound of Chemical Formula 5 was dissolved in 1,000 ml of methylene chloride (MC) by stirring. After the reactor was cooled to 0° C., 30.26 g (0.2991 mol) of triethylamine (TEA) was slowly added to the reactor and stirred for about 30 min. The reactor was further cooled to −15° C., after which 32.46 g (0.2991) of ethylchloroformate (ECF) was loaded to the reactor over about 1 hr through a dropping funnel under the same temperature condition. Then, the temperature of the reactor was elevated to −2~0° C. at which a reaction was allowed to proceed for about 2 hrs to give the compound of Chemical Formula 10.

In a separate 1 L reactor, 75.0 g (0.2991 mol) of the compound of Chemical Formula 14, 500 ml of MC, and 30.26 g (0.2991 mol) of TEA were mixed for about 30 min by stirring, and the mixture was transferred to a dropping funnel (Chemical Formula 14 solution).

To the 3 L reactor which was further cooled to −15° C., the Chemical Formula 14 solution (free salt) was slowly added over about 4 hrs, and stirred. The temperature was elevated to room temperature before they were reacted overnight. After completion of the reaction, the reaction mixture was washed with distilled water, 1N HCl, 0.5N NaHCO₃, and distilled water in that order. The aqueous layer was discarded, and the pooled MC layer was dehydrated, and concentrated by distillation to obtain a crude compound of Chemical Formula 15 (141.5 g, 100%). This product was crystallized with ethyl acetate (EA) and n-hexane, and filtered to afford the compound of Chemical Formula 15 (130.1 g, yield 92%).

TABLE 4

Material Balance and Theoretical Yield of Chemical Formula 15 and Ramalin (Chemical Formula 1)

| Exp. No. | MW | Q'TY | Moles | Remark |
| --- | --- | --- | --- | --- |
| Chemical Formula 5 | 371.38 | 92.58 | 0.2493 | |
| TEA | 101.19 | 30.26 | 0.2991 | d: 0.726 |
| ECF | 108.52 | 32.46 | 0.2991 | d: 1.1408 |
| Chemical Formula 14 | 250.72 | 75.0 | 0.2991 | |
| TEA | 101.19 | 30.26 | 0.2991 | |
| Chemical Formula 15 | 567.63 | 141.51 | 0.2493 | 100% Yield |
| Chemical Formula 1 | 253.25 | 63.13 | 0.2493 | 100% Yield |

Figure 4:
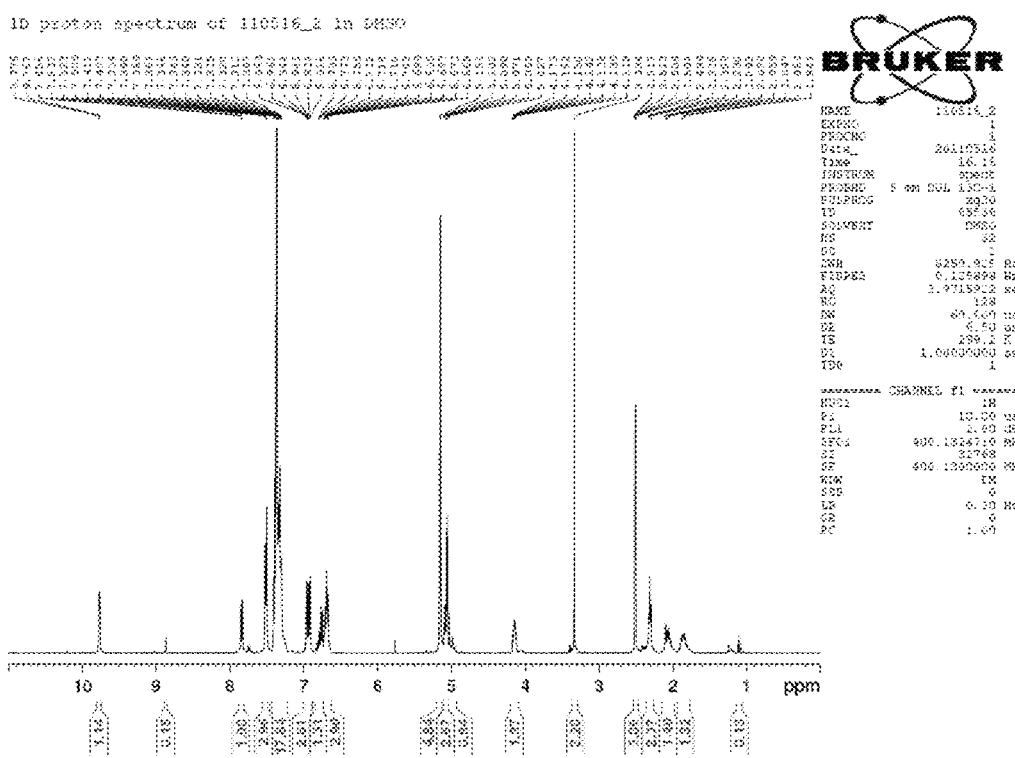
FIG. 4 is an H-NMR spectrum of the compound of Chemical Formula 15.

H-NMR data of the compound of Chemical Formula 15 are given in FIG. 4.

To a pressure reactor were added 80.0 g (0.14 mol) of the compound of Chemical Formula 15, 800 ml of methanol, and 8.0 g of 10% Pd/C, and the pressure of the reactor was controlled to 10~20 psi with hydrogen. Debenzylation was conducted for 24 hrs. After the reaction was completed when a sample taken from the reactor was monitored, the catalyst was removed by filtration, and the filtrate was concentrated in a vacuum to give a crude compound (Chemical Formula 1) (35.45 g, 100%). The concentrate was added to 500 ml of EA and mixed sufficiently for about 2 hrs or longer to produce crystals. They were filtered, and dried to afford the final product ramalin (Chemical Formula 1) (32 g, yield 90.2%).

The experiment described above was repeated five times in total, and the results are summarized in Table 5, below.

TABLE 5

Results of 5 Rounds of Experiment

| EXP. No. | 100% Yield wt. (g) | Product Weight (g) | Yield (%) |
|---|---|---|---|
| 001 | 35.68 | 32.6 | 91.3 |
| 002 | 35.68 | 32.7 | 91.8 |
| 003 | 91.45 | 82.0 | 92.0 |
| 004 | 49.07 | 45.0 | 91.7 |
| 005 | 35.45 | 32.0 | 90.2 |

Figure 5:
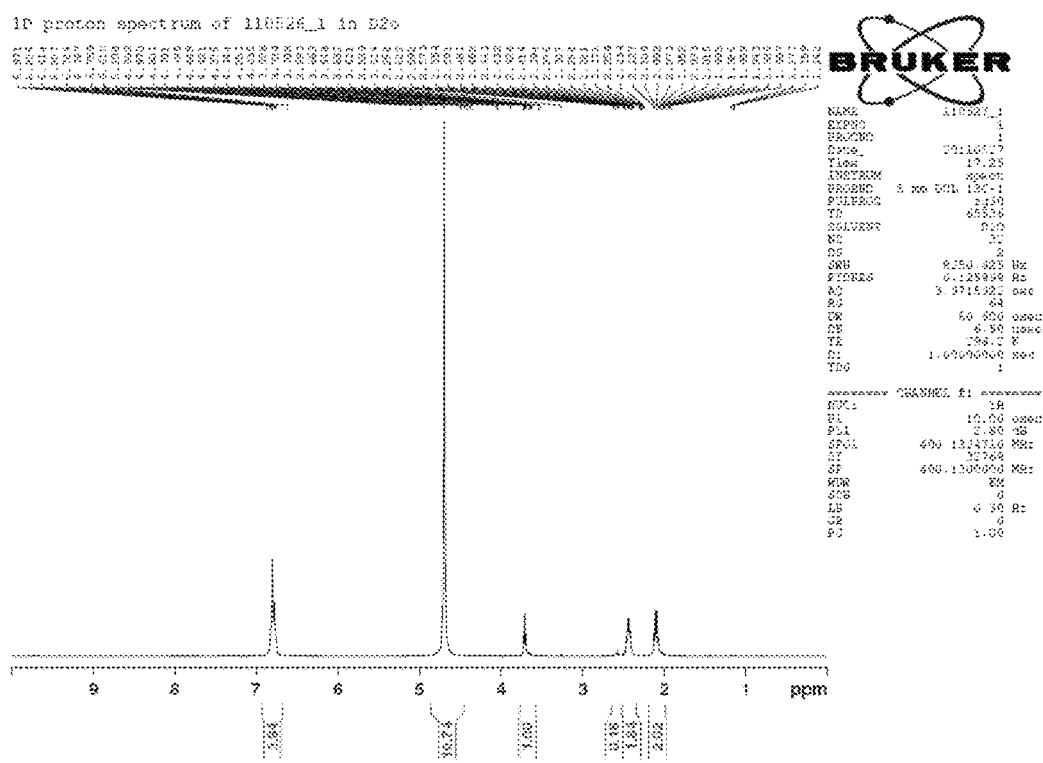
FIGS. 5 and 6 are H-NMR spectra of the ramalin synthesized in Example 2.
Figure 6:
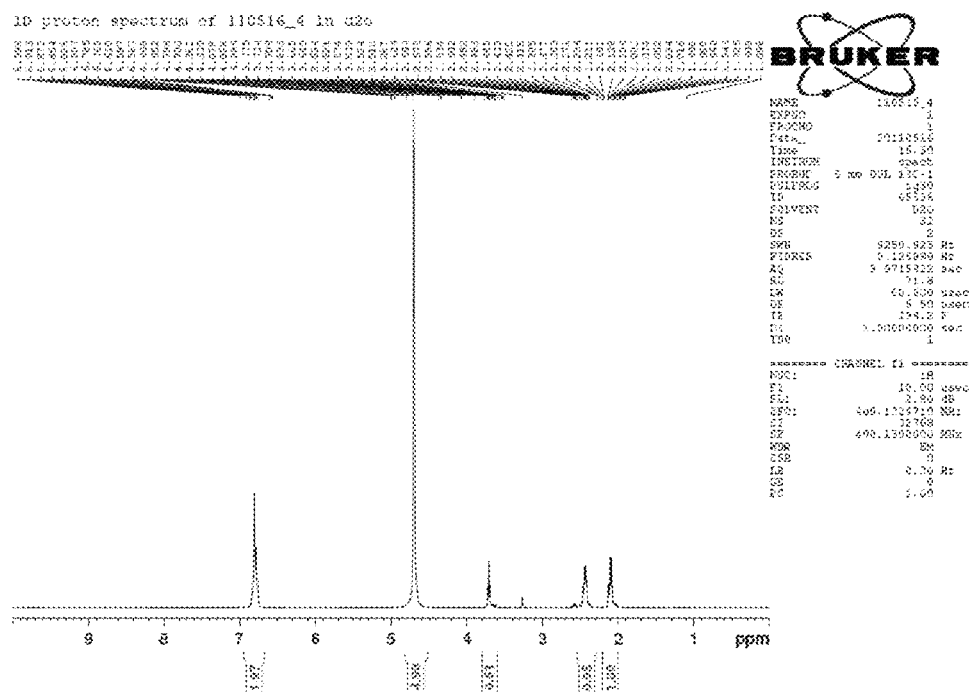

As can be seen in Table 5, the ramalin of Chemical Formula 1 was prepared at a mean yield of about 90~92%, and results were identified using H-NMR data (FIGS. 5 and 6).

INDUSTRIAL APPLICABILITY

As described above, the synthesis method of the present invention allows ramalin, excellent in antioxidant and anti-inflammatory activity, to be simply synthesized at stable yield even without such a highly toxic solvent as DMF. In addition, the method of the present invention is cost competitive, and provides ramalin at high efficiency, thus enabling the mass production of ramalin.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of synthesizing ramalin, comprising:
   (a) producing a compound represented by Chemical Formula 4 by reacting a glutamic acid derivative represented by the following Chemical Formula 2 with a hydrazine salt compound represented by the following Chemical Formula 3; and
   (b) producing the ramalin represented by Chemical Formula 1 by hydrogenating the compound of Chemical Formula 4:

[Chemical Formula 1]

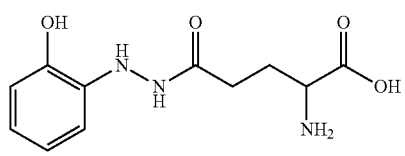

[Chemical Formula 2]

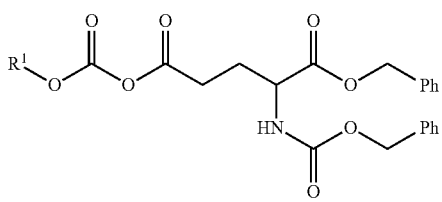

[Chemical Formula 3]

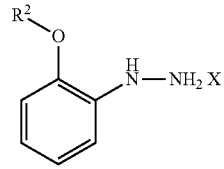

[Chemical Formula 4]

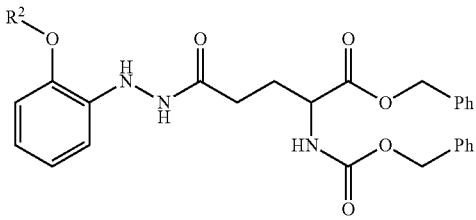

wherein,
R$^1$ is alkyl;
R$^2$ is hydrogen or a hydroxy protecting group; and
X is an acid.

2. The method of claim 1, wherein the glutamic acid derivative represented by Chemical Formula 2 is prepared by reacting a glutamic acid derivative represented by Chemical Formula 5 with alkylchloroformate having a structure of R$^1$—O—CO—Cl:

[Chemical Formula 5]

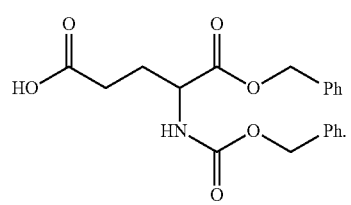

3. The method of claim 2, wherein the glutamic acid derivative represented by Chemical Formula 5 is prepared by protecting an amino acid group of the glutamic acid with a carbobenzyloxy group, and esterifying an alpha carboxyl group with a benzyl group.

4. The method of claim 1, wherein the hydrazine salt compound represented by Chemical Formula 3 is prepared by reducing azo compound from 2-hydroxy aniline or an acid salt of protected hydroxy aniline.

5. The method of claim 1, wherein R$^1$ is selected from the group consisting of methyl, ethyl, propyl, isopropyl, butyl, isobutyl, pentyl, hexyl, heptyl, octyl, 2-ethylhexyl, substituted alkyl, and cycloalkyl.

6. The method of claim 1, wherein R$^1$ is ethyl.

7. The method of claim 1, wherein R$^2$ is hydrogen.

8. The method of claim 1, wherein R$^2$ is a benzyl group for protecting hydroxy.

9. The method of claim 1, wherein the acid is hydrochloric acid, bromic acid, iodic acid, or P-toluenesulfonic acid.

10. A method of synthesizing a ramalin precursor, comprising reacting a glutamic acid derivative represented by the following Chemical Formula 2 with a hydrazine salt compound represented by the following Chemical Formula 3, thereby producing the ramalin precursor represented by the following Chemical Formula 4:

[Chemical Formula 2]

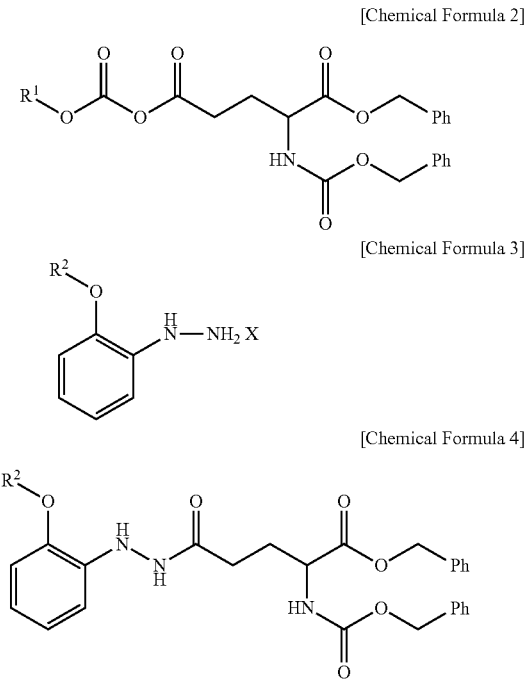

[Chemical Formula 3]

[Chemical Formula 4]

wherein,
R¹ is alkyl;
R² is hydrogen or a hydroxy-protecting group; and
X is an acid.

11. The method of claim 10, wherein the glutamic acid derivative of Chemical Formula 2 is prepared by reacting a glutamic acid derivative represented by the following Chemical Formula 5 with alkylchloroformate having a structure of $R^1$—O—CO—Cl:

[Chemical Formula 5]

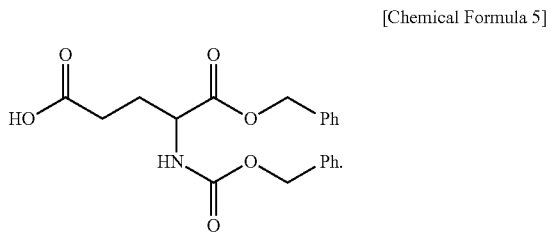 [SMILES: O=C(O)CCC(NC(=O)OCc1ccccc1)C(=O)OCc1ccccc1]

12. A method of synthesizing a compound of Chemical Formula 16, comprising reacting an amino acid derivative represented by the following Chemical Formula 17 with a hydrazine salt compound represented by the following Chemical Formula 18:

[Chemical Formula 16]

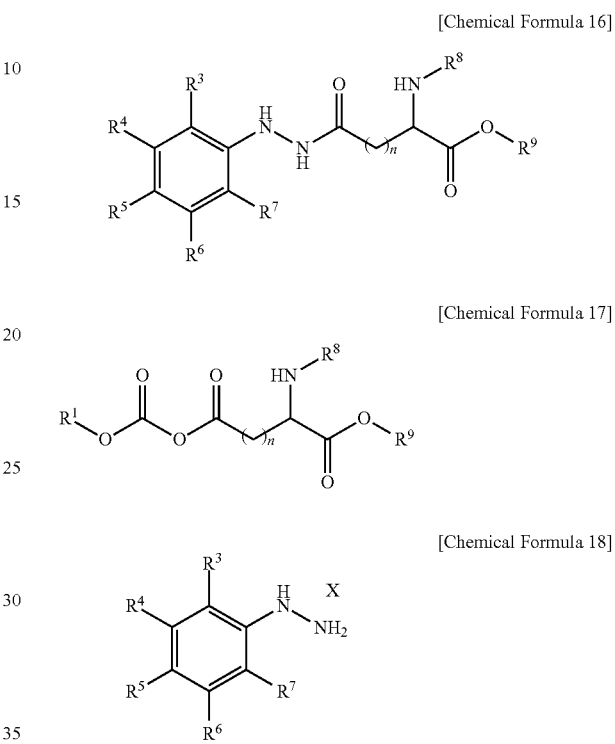

[Chemical Formula 17]

[Chemical Formula 18]

wherein,
$R^3$, $R^4$, $R^5$, $R^6$, and $R^7$ are each independently hydrogen, a hydroxyl group or a hydroxyl alkyl group;
$R^8$ is hydrogen, an alkyl group or an acyl group;
$R^9$ is hydrogen or an alkyl group; and
n is 1, 2, 3, 4 or 5.

* * * * *

UNITED STATES PATENT AND TRADEMARK OFFICE
CERTIFICATE OF CORRECTION

PATENT NO. : 9,284,266 B2
APPLICATION NO. : 14/372787
DATED : March 15, 2016
INVENTOR(S) : Joung Han Yim et al.

It is certified that error appears in the above-identified patent and that said Letters Patent is hereby corrected as shown below:

Specification

Column 3, line 4: "represented by the M following" should be -- represented by the following --.

Signed and Sealed this
Nineteenth Day of July, 2016

Michelle K. Lee
*Director of the United States Patent and Trademark Office*